US012576108B2

(12) United States Patent
  Koruga

(10) Patent No.: US 12,576,108 B2
(45) Date of Patent: Mar. 17, 2026

(54) COMPOSITIONS COMPRISING HYPER HARMONIZED HYDROXYL MODIFIED FULLERENE SUBSTANCES

(71) Applicant: Fieldpoint (Cyprus) Limited, Nicosia (CY)

(72) Inventor: Djuro Koruga, Belgrade (RS)

(73) Assignee: FIELDPOINT (CYPRUS) LIMITED, Nicosia (CY)

( * ) Notice: Subject to any disclaimer, the term of this patent is extended or adjusted under 35 U.S.C. 154(b) by 727 days.

(21) Appl. No.: 17/756,672

(22) PCT Filed: Dec. 2, 2019

(86) PCT No.: PCT/EP2019/083307
  § 371 (c)(1),
  (2) Date: May 31, 2022

(87) PCT Pub. No.: WO2021/110234
  PCT Pub. Date: Jun. 10, 2021

(65) Prior Publication Data
  US 2022/0409658 A1     Dec. 29, 2022

(51) Int. Cl.
  *A61K 33/44*      (2006.01)
  *A61K 31/375*     (2006.01)
(52) U.S. Cl.
  CPC ............ *A61K 33/44* (2013.01); *A61K 31/375* (2013.01)
(58) Field of Classification Search
  None
  See application file for complete search history.

(56) References Cited

U.S. PATENT DOCUMENTS 8,058,483 B2    11/2011  Koruga

FOREIGN PATENT DOCUMENTS

| JP | 2011504456 A | 2/2011 |
|----|--------------|--------|
| WO | 01/24696 A1 | 4/2001 |
| WO | 2008/097922 A2 | 8/2008 |

OTHER PUBLICATIONS

Examination Report issued by the Canadian Patent Office for application No. 3,159,140, dated Jul. 25, 2023.
International Preliminary Report on Patentability issued in PCT application No. PCT/EP2019/083307, date of issuance May 17, 2022.
Notice of Reasons for Rejection issued by the Japanese Patent Office in application No. P2022-532088, dated Jun. 30, 2023.
English translation of Notice of Reasons for Rejection issued by the Japanese Patent Office in application No. P2022-532088, dated Jun. 30, 2023.
International Search Report and Written Opinion issued in PCT/EP2019/083307, dated Apr. 20, 2020.
Miljkovic et al., "Influence of hyper-harmonized fullerenc water complex on collagen quality and skin function", 2019 Wiley Periodicals, Inc., J Cosmet Dermatol. 2020; 19; 494-501.
Examination Report issued by the Canadian Patent Office for application No. 3,159,140, dated Jun. 4, 2024.
Office Action issued by the Australian Patent Office in application No. 2019476738, and dated Feb. 22, 2023.

*Primary Examiner* — Bennett M Celsa
*Assistant Examiner* — Edwin Coleman Mitchell
(74) *Attorney, Agent, or Firm* — Barnes & Thornburg LLP; Jeffrey R. Stone

(57) ABSTRACT

The present invention relates to hyper harmonized hydroxyl-modified fullerenes, hydroxyl-modified fullerenes in a suitable carrier, and hydroxyl-modified fullerene formulations including a suitable carrier with optional additives. These compositions of matter and formulations have numerous applications including, for example, the cosmetic industry, dietary supplements, food industry, plants and healthcare fields.

13 Claims, 9 Drawing Sheets

FIG.1a
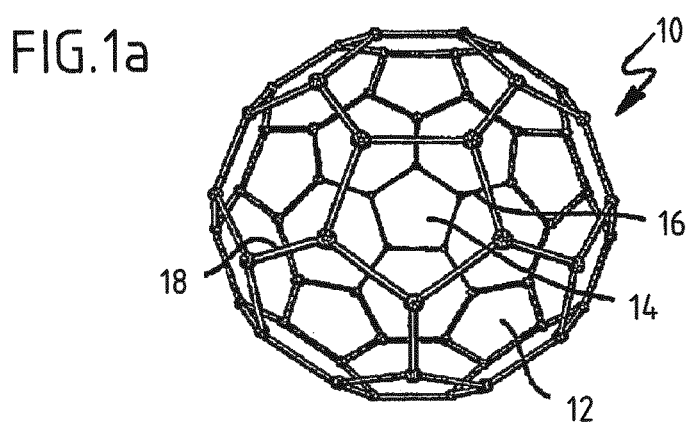
FIG.1b
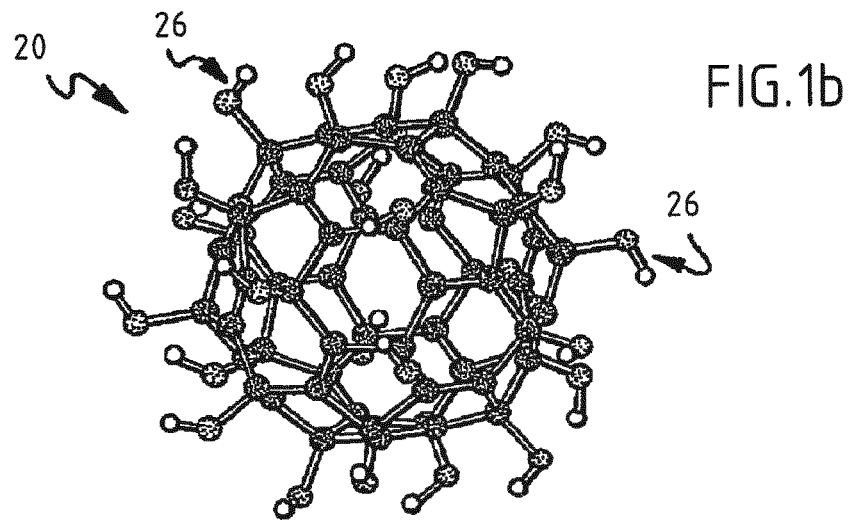
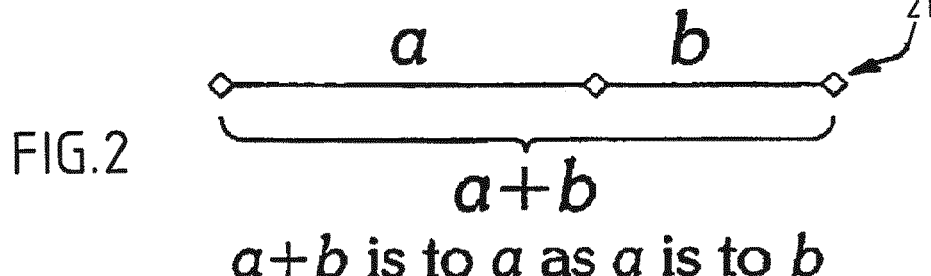
FIG.2
$a+b$ is to $a$ as $a$ is to $b$

Spectra of UV light on which is applied on skin (λ=375 nm)

Spectra of UV light on skin through cream base

Spectra of UV light is applied on skin through classical cream

Spectra of UV light influence on skin through cream with 3HFWC

• UV shift
  380 nm to 390 nm

• Transform UV light
  into visible spectra

• Skin looks better
  (little whiter)

Hand cream with 3HFWC substance
Basal membrane level (p+/p-)          Epidermis + dermis (p+/p-)
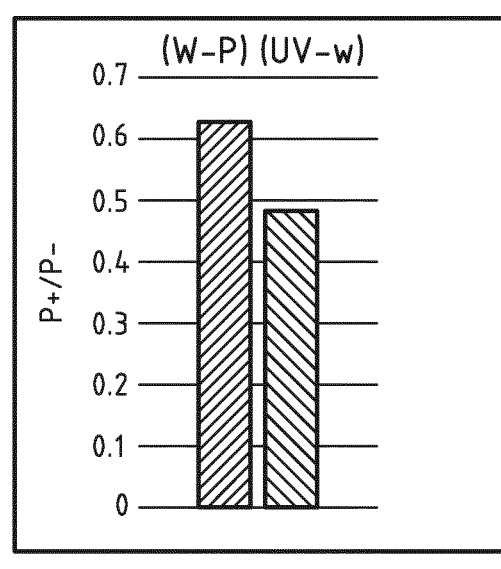
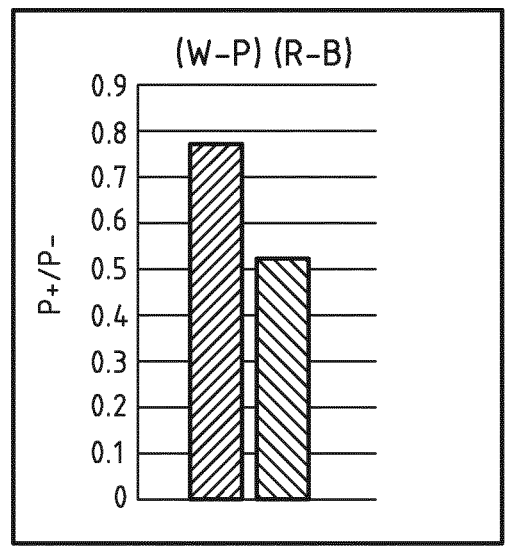
◨ Before Treatment          ▨ Before Treatment
▨ After Treatment           ◨ After Treatment
FIG.11A                     FIG.11B

COMPOSITIONS COMPRISING HYPER HARMONIZED HYDROXYL MODIFIED FULLERENE SUBSTANCES

The present invention relates to hyper harmonized hydroxyl-modified fullerenes, hydroxyl-modified fullerenes in a suitable carrier, and hydroxyl-modified fullerene formulations including a suitable carrier with optional additives. These compositions of matter and formulations have numerous applications including, for example, the cosmetic industry, dietary supplements, food industry, plants, and healthcare fields.

The importance of hydrogen bonding in the structure and function of biological macromolecules was predicted by the earliest investigators (Pauling, Corey, and Branson, 1951). According to Linus Pauling, the first prediction of the existence of a hydrogen bond should be attributed to M. L. Huggins in 1919 and independently to W. M. Latimir and W. H. Rodebush in 1920. Bearing in mind that most biological systems contain water from 60% to 80%, the importance of hydrogen bonds has become most relevant for understanding how biomolecular machinery, as a complex system, works. Within a collection of water molecules, the hydrogen atom is covalently bound to an oxygen atom in the water molecule and hydrogen bonds with oxygen atoms on separate water molecules. It is well known that covalent bonds may only be described by quantum mechanics, because each electron does not really belong to a single atom—it belongs to both simultaneously. For a long period of time, scientists believed that the hydrogen bond could be perfectly understood by the principles of electrostatic interactions using Coulomb's law (pre-20$^{th}$ century classical physics), based on the attraction and repulsion between charged particles separated from each other by a distance.

However, recent experimental data indicates that a hydrogen bond has double identity: classical and quantum (Isaacs, 1999, Barbiellini, and Shukla, 2003). This is the key point for understanding a new approach to explaining how DNA and proteins function in water. It is believed that water itself may be a coding structure, via its hydrogen bonds, if some water molecules are organized in clusters and some of them are ordered in interconnected chains between water clusters by Fibonacci law. Some local domains of water, under the influence of DNA and microtubules, may be responsible for organizing water molecules into clusters as complementary coding forms. 40% of the water within a human is free water, while 60% of the water is captured by biomolecules. Estimates predict that only 5% of free water is in clusters organized by a sphere packing law of coding number 12. The remaining 95% of free water is in the form of "chaos" with local polymerized islands.

According to a coding approach based on sphere packing analysis, the optimal molecular organization of water molecules should be as a hydrogen-bonded $(H_2O)_n$ polyhedra $5^{12}6^n$ (n=0, 2, 4 . . . ), where $5^{12}$ represents 12 pentagons and n different number of hexagons (Jeffrey, 1997). Through hydrogen bonds dynamics, this polyhedra-shaped structure of water molecules possesses a spherical coding system $2^5=32$. The arrangement of water molecules, based on number 12, may represent a coding system which is part of an optimal information peak of sphere packing (Sloane 1984, Koruga, 1986). Accordingly, water hydrogen-bonded polyhedra is both compatible and complementary with the coding system of the genetic code (DNA and proteins).

An understanding of the hydrogen bonding dynamic on quantum chemical scales is useful in the study of biological systems, including the study of diseases, such as cancer or other medical conditions, and cosmetic conditions related to the human skin. Such understanding is also useful for dietary supplements, food industry, plants, etc. By way of background with regard to the human skin, the epidermis is a dynamic renewing structure that provides life-sustaining protection from the environment. Keratinocytes and melanocytes are the major cell types responsible for the structure of the epidermis. Keratinocytes and melanocytes begin as stem cells in the basal epidermal layer. As keratinocytes move to the epidermal surface, the cells cease cell division and undergo morphological changes to form the prickle or spinous cells, granular cells, transition cells, keratinized squames, and surface squames. One melanocyte cell may overlap a few keratinocytes giving them melanin (mechanism is yet unknown), which is responsible for protection of the environmental electromagnetic radiation (UV radiation) and neutralization of free radicals (Varni et al, 2004 van den Bossche, at al. 2006).

It is also well known that vitamin C (L-ascorbic acid) can be used in the treatment of conditions related to the skin. One of the major roles of vitamin C is its stimulation effects on collagen synthesis without affecting other protein synthesis. Vitamin C is a desired component of cosmetic products for both proline and lysine hydroxylase, which stabilize the collagen molecule. This reaction is necessary for skin to maintain its strength.

Also, collagen distortion below the base level membrane (lamina fibroreticularis) occurs when cancer penetrates through the epidermis into the dermis, and "opens the door" for metastases. From a classical communication channels point of view, gene expression is responsible for it: normal collagen, type I $[\alpha1(I)_2\alpha2(I)]$, comprises two procollagen chains, the first $\alpha1(I)$ (gene located on chromosome 17 (q21-q22)), and the second procollagen chain $\alpha2(I)$ (gene located on chromosome 7(q21-q22)). According to quantum theory, quantum communication channels exist among keratinocyte or melanocyte and fibroblast cells (entanglement) based on hydrogen bonding in the DNA.

When symmetry-breaking of hydrogen bonds happens in DNA, then automatically, through DNA-microtubule-water coding entanglement, synergy of classical and quantum communication is broken. There is experimental evidence that fibroblast cells and human melanoma cells interact with tumor cell growth as a function of tumor progression (Coinil, at. al. 1991). If UV radiation damages DNA on chromosome 7, in keratinocyte or melanocyte cells, then through non-classical quantum channels this information will transfer to both centriole (damaged cell) and fibroblast cells in the region. The centriole will become "wild" (from bipolar mitosis change to three polar or multipolar mitosis) and will start to divide chromosomes irregularly. The nucleus of an initial cancer cell will grow faster than normal cells. The "wild" cell will be duplicated and rapidly increase in number because positive feedback control mechanism water-centriole will change perpendicularly to centriole pairs (Koruga, et. al. 1992).

From another side, fibroblast cells will cease synthesizing collagen $\alpha2(I)$. In the absence of $\alpha2(I)$, procollagen chains during assembly into procollagen molecules, will incorporate an additional $\alpha1(I)$ procollagen chain. This will give collagen type I-trimer with a structure $[\alpha1(I)_3]$. The I-trimer links between procollagen chains do not fit well, and OH groups will be removed from collagen to make free water molecules. The volume of free water will increase from 20% in tissue (Foster and Schwan, 1986). A similar occurrence is observed in skin aging and accounts for the reason for people to have an increased risk of cancer as they age (Richard, at. al., 2004).

When this type of collagen becomes dominant in a given tissue, the lamina fibroreticularis becomes weak, because the interconnection between procollagen chains in procollagen molecules, based on hydrogen bonds, is not adequate (the electromagnetic shield of a basal membrane has holes). Then, a mass of skin cancer or melanoma, can penetrate the basal lamina and reach the superficial arteriovenous plexus (Brinkley, 2001).

Hydrogen bonding in biomolecule networks in cell and tissue, as well as their complex intermolecular connections, resemble spider webs. It is a link between classical and quantum behavior of matter on a molecular level, and it is a basic element of synergy between mass-energy and information in living matter.

DNA is coded by $4^{th}$ perfect number code $2^n(2^{n+1}-1)$ with 8128 code words, which is responsible for protein coding (classical) and system complexity coding (quantum) by entanglement (Koruga, 2005, Koruga, et al. 2006). There is mapping one-to-one from genetic code to proteins by synergetic code. There is synergetic code (classical/quantum) in protein chain based on amino acids and peptide plains. Hydrogen bonds are links between classical and quantum behaviours of matter on a molecular level, and it is a basic element for synergy of mass-energy-information in living matter.

Understanding DNA as a synergetic classical/quantum device, based on a golden mean and the fourth perfect number, may help to find methods for prevention and healing of many illnesses. Bearing in mind that proteins are the second side of DNA code, interaction and communication of DNA and protein may be both through separate classical and quantum communications channels, and through synergetic one.

DNA and water exist in a very delicate relationship. In normal situations, DNA operates in accordance with the fourth perfect number law, while water operates in accordance with the third perfect number law, i.e. 496 code words. In normal situations, the DNA-water system works harmonically. However, when, for some reason, DNA collapses from operating in accordance with the fourth perfect number law to the third perfect number law, then information about the disharmonic state of DNA travels more smoothly and faster through water than its harmonic one.

The object of the present invention is directed to hyper harmonized hydroxyl-modified fullerenes and an optional suitable carrier. These compositions of matter and formulations have numerous applications including, for example, the cosmetic industry, dietary supplements, food industry, plants, and healthcare fields.

These objects have been achieved by the compositions of the invention, as described in the following.

In a first aspect, the present invention relates to a composition comprising:
a hyper harmonized [$D_4$ ($\Phi/\phi$)] form of a hydroxyl modified fullerene having a molecular formula of $C_{60}(OH)$ $_xH_y\forall_z$ (where x is from 24 to 48, and y is from 0 to 24 and z is from 0 to 12); and
 a plurality of water layers surrounding the harmonized form of the hydroxyl modified fullerene; wherein the plurality of water layers comprises from 4 water layers to 10 water layers.

In another aspect, the present invention relates to a method of preparing a hyper harmonized [$D_4$ ($\Phi/\phi$)] form of a hydroxyl modified fullerene having a molecular formula of

4

$C_{60}(OH)_xH_y\forall_z$ (where x is from 24 to 48, and y is from 0 to 24 and z is from 0 to 12); wherein the method comprises:
 adding a hydroxylated fullerene to ultra-pure water (e.g. water with an electrical resistance ranging from 0.05 μS/cm to 0.7 μS/cm, preferably with an electrical resistance of 18.2 MΩ) to form a mixture;
 applying an oscillating magnetic field to the mixture at a temperature ranging from 34 C to 42 C; wherein the magnetic force ranges from 0.2 T to 1.8 T, preferably from 0.4 T to 1.2 T; and
forming a composition comprising a hyper harmonized form of a hydroxyl modified fullerene having a plurality of water layers surrounding the hyper harmonized form of the hydroxyl modified fullerene; wherein the plurality of water layers comprises from 4 water layers to 10 water layers.

In various embodiments, the oscillating magnetic field is applied for a period of time ranging from 54 minutes to 90 minutes, preferably from 72 minutes to 81 minutes. The period of time may be divided into 6 sessions where a first session of the oscillating magnetic field is applied at +0.5 T according to:

$$D_4 = \begin{bmatrix} 1 & 2 & 3 & 5 \\ 8 & 13 & 21 & 34 \\ 55 & 89 & 144 & 233 \\ 377 & 610 & 987 & 1597 \end{bmatrix} = 0$$

(hereinafter referred to as "$D_4$ rule").

A second session of the oscillating magnetic field is applied at −0.5 T; a third session of the oscillating magnetic field is applied at +0.5 T; a fourth session of the oscillating magnetic field is applied at −0.5 T; a fifth session of the oscillating magnetic field is applied at +0.5 T; a sixth session of the oscillating magnetic field is applied at −0.5 T. For example, the period of time may be 54 minutes, and each session may be 9 minutes each. In alternative embodiments, one or more sessions may have a different period of time than a preceding session.

Further embodiments are defined in the appended claims.

In the drawings, like reference characters generally refer to the same parts throughout the different views. The drawings are not necessarily to scale, emphasis instead generally being placed upon illustrating the principles of the illumination apparatus. In the following description, various aspects are described with reference to the following drawings, in which:

FIG. 1 *a* is a diagrammatic view of a $C_{60}$ fullerene molecule;

FIG. 1 *b* is a diagrammatic view of a $C_{60}(OH)_{24}$ molecule;

FIG. 2 is a diagrammatic representation of a Golden Mean Rule in one dimension;

FIG. 3 *a* is a diagrammatic view of general internal hydrogen bonding in a protein 24 (healthy bonding);

FIG. 3 *b* is a diagrammatic view of external hydrogen bonding in a protein 24 (unhealthy bonding);

Figure 6:
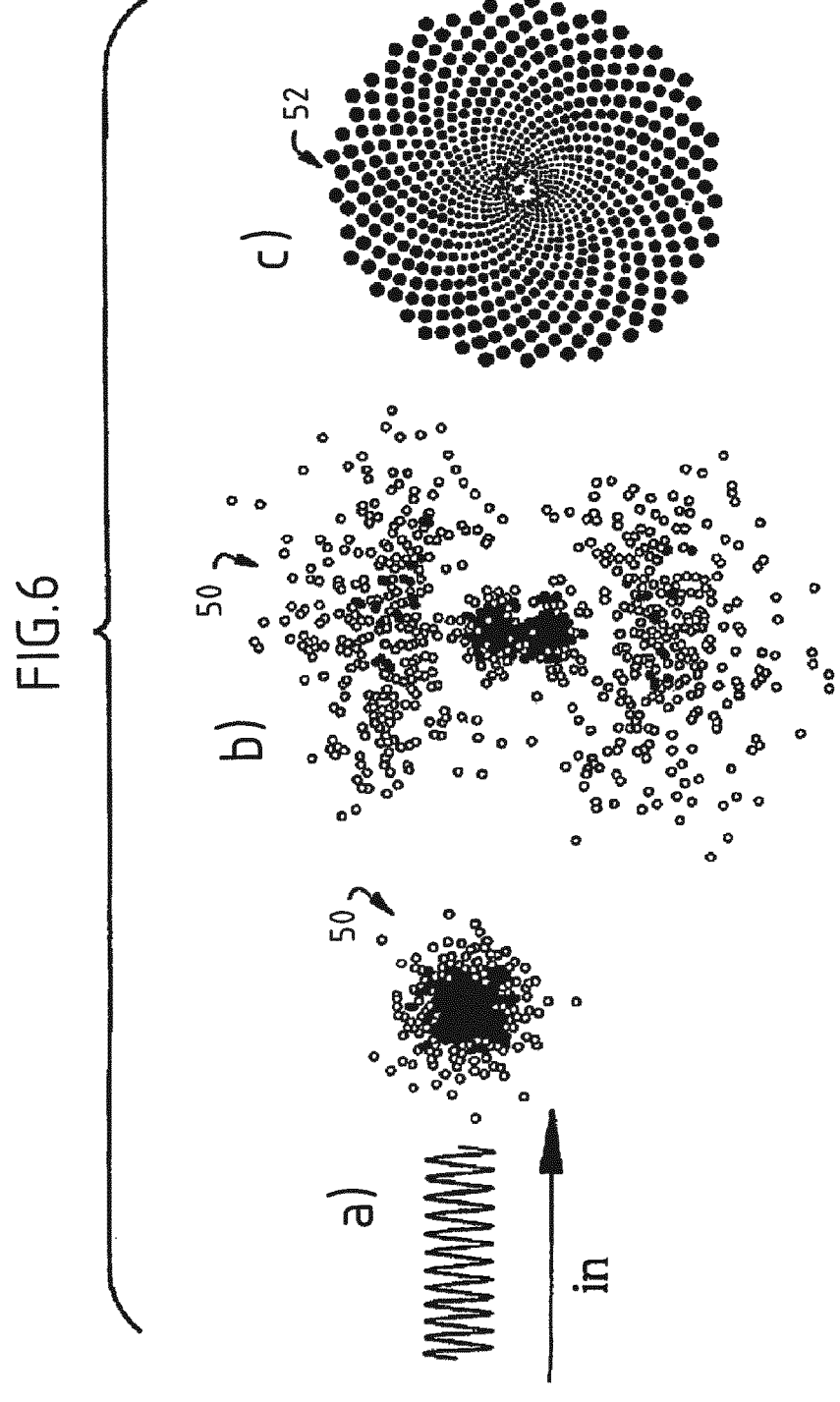

FIG. 6 *a* is a diagrammatic representation of a cluster of electrons in the ground state;

FIG. 6 *b* is a diagrammatic representation of the cluster of electrons in an excited state resulting from applying energy to the electron cluster shown in FIG. 6 *a;*

Figures 7, 8:
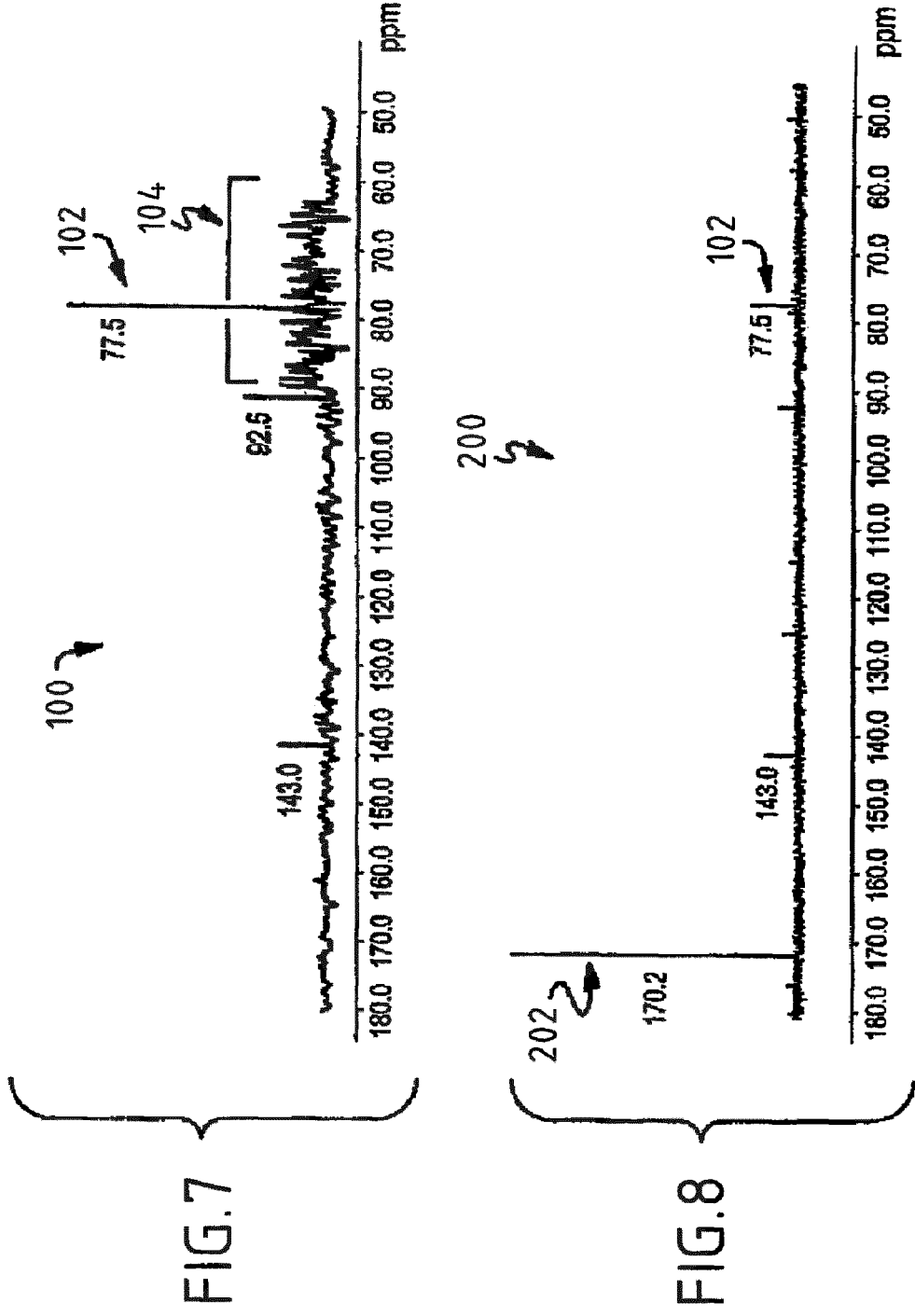
Figure 9:
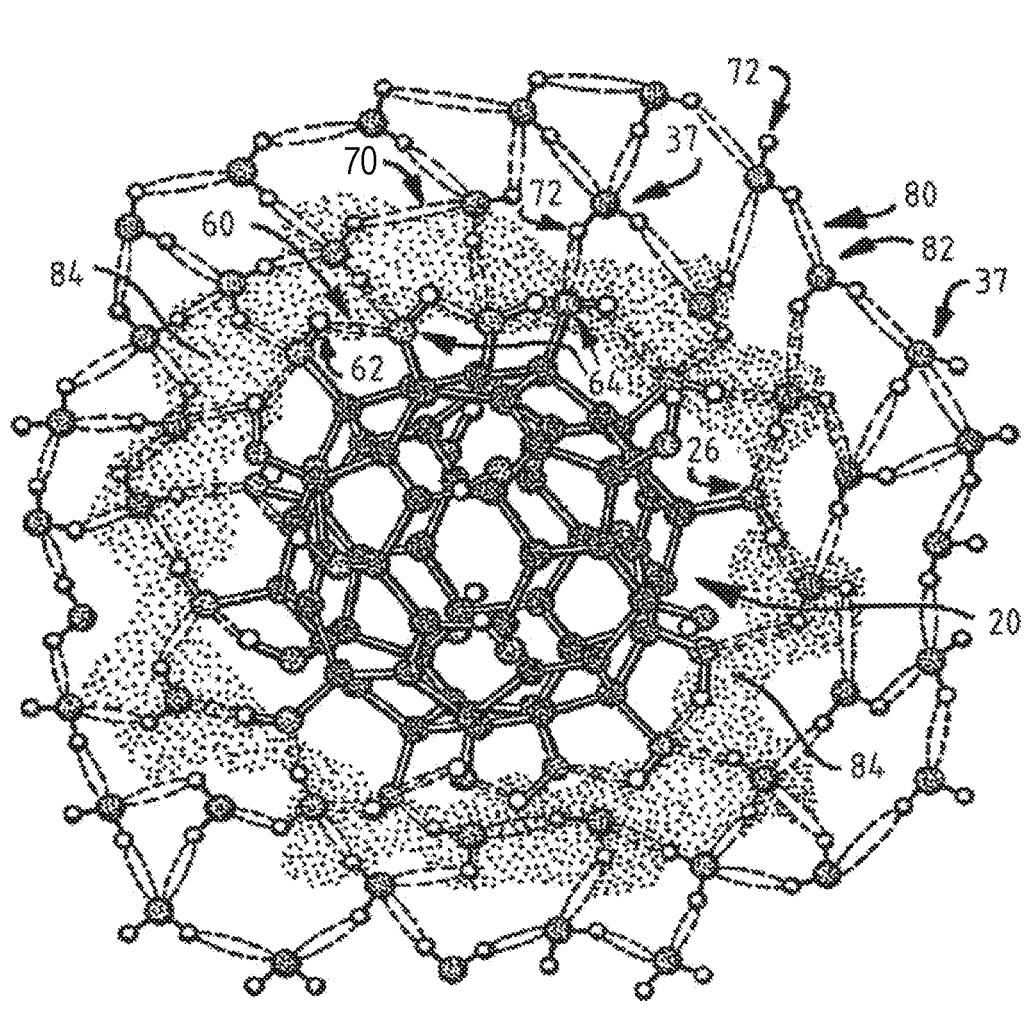

FIG. 6 *c* is a diagrammatic representation of an electron cloud in an excited state forming a sunflower pattern as a result of subjecting the electron cluster of FIG. 6 *a* to a harmonization process;

FIG. 7 is a $^{13}C$ NMR spectra for a hydroxyl modified fullerene $C_{60}(OH)_{24}$;

FIG. 8 is a $^{13}C$ NMR spectra for a harmonized, hydroxyl modified fullerene $[C_{60}(OH)_{10-36}]^{D3[\Phi/\varphi]}$; and FIG. 9 is a diagrammatic view of a $C_{60}(OH)_{24}$ in water showing three levels of hydrogen bonding.

Figure 10A:
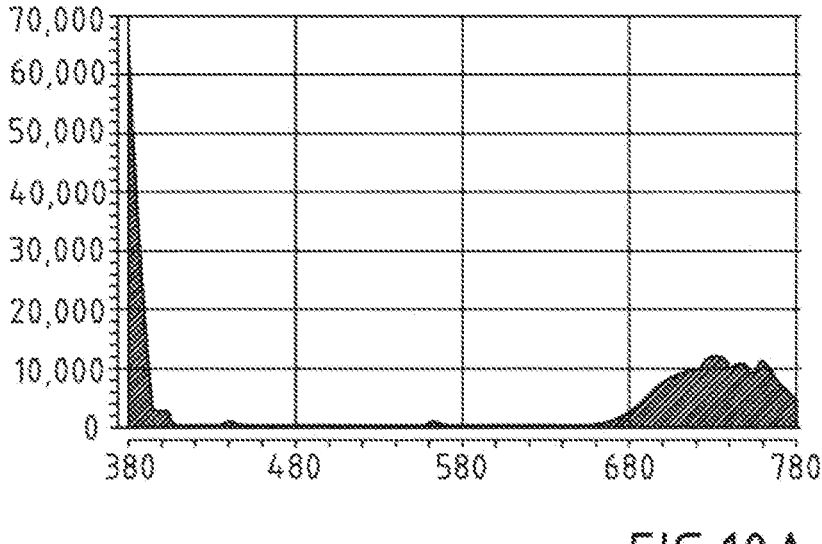

FIG. 10A is a graph representing ultraviolet measurements taken after various treatments were applied to human skin.

Figure 10B:
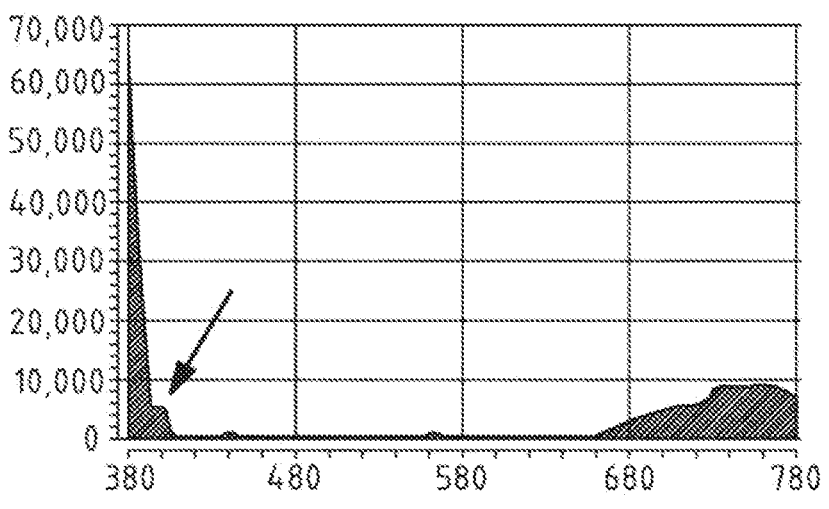

FIG. 10B is a further view of a graph representing ultraviolet measurements taken after various treatments were applied to human skin.

Figure 10C:
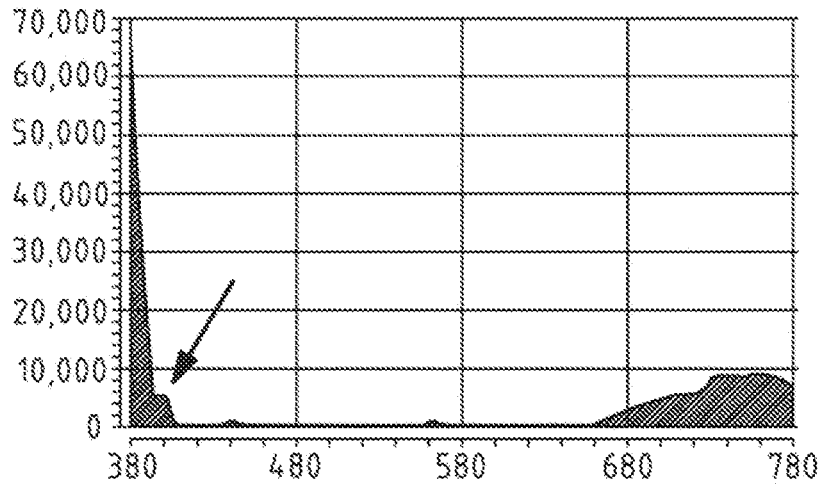

FIG. 10C is a further view of a graph representing ultraviolet measurements taken after various treatments were applied to human skin.

Figure 10D:
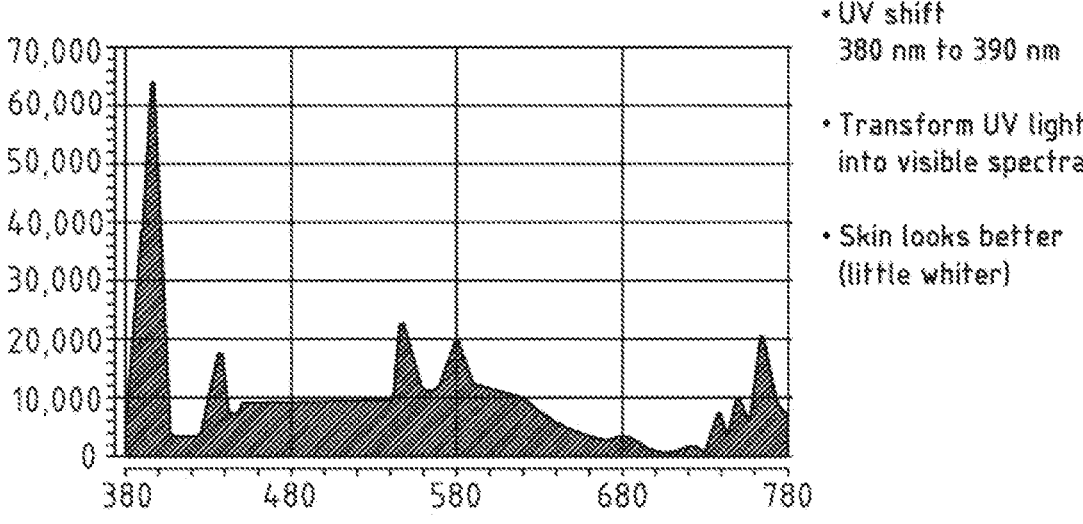

FIG. 10D is a further view of a graph representing ultraviolet measurements taken after various treatments were applied to human skin.

FIG. 11A is a graph representing paired and unpaired electrons in the skin tissue before and after treatment.

FIG. 11B is a further view of a graph representing paired and unpaired electrons in the skin tissue before and after treatment.

Figure 12:
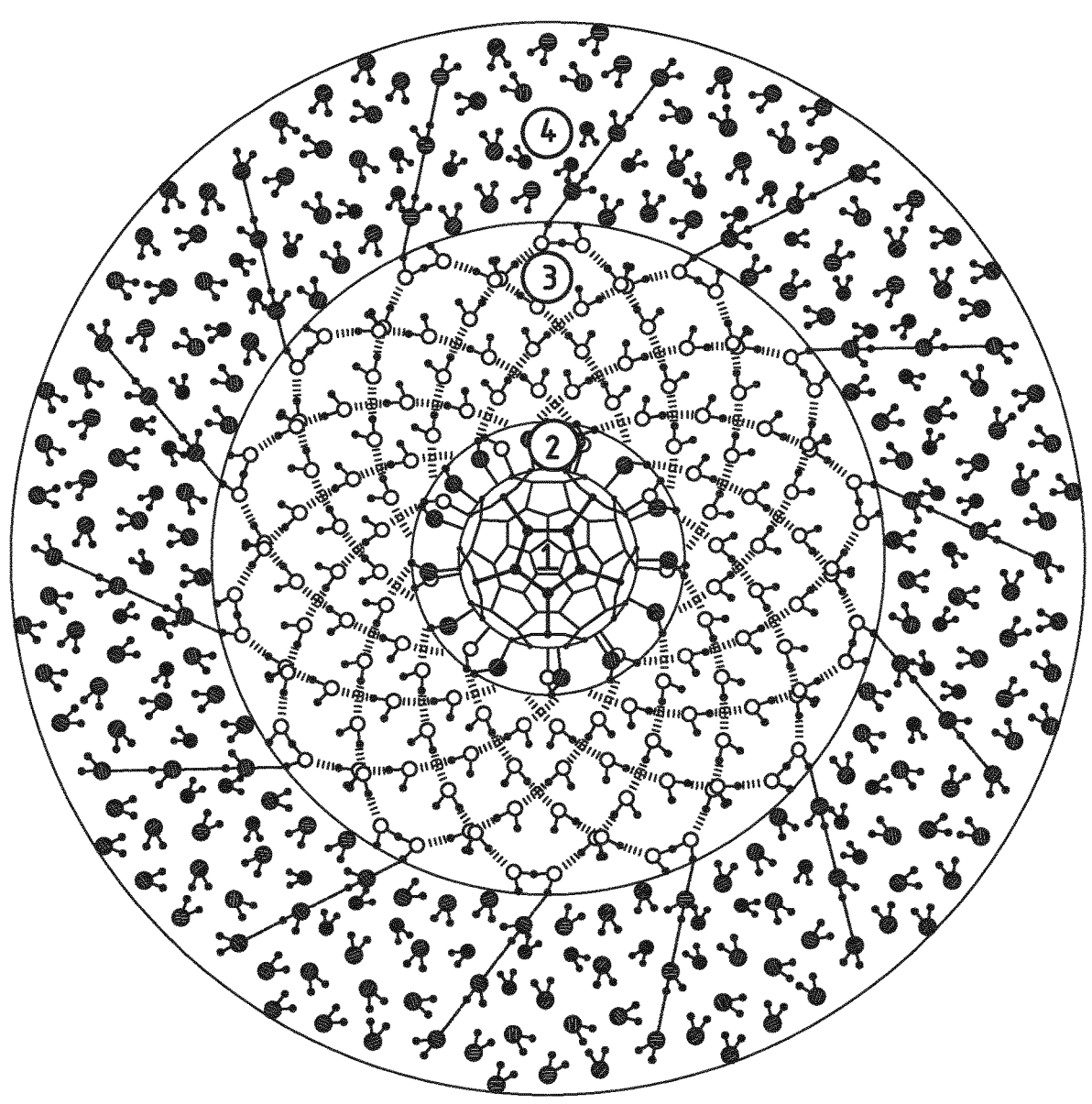

FIG. 12 illustrates a hyper harmonized hydroxyl modified fullerene and how it functions in its environment.

"One or more", as used herein, relates to at least one and comprises 1, 2, 3, 4, 5, 6, 7, 8, 9 or more of the referenced species. Similarly, "at least one" means one or more, i.e. 1, 2, 3, 4, 5, 6, 7, 8, 9 or more. "At least one", as used herein in relation to any component, refers to the number of chemically different molecules, i.e. to the number of different types of the referenced species, but not to the total number of molecules.

In the present specification, the terms "a" and "an" and "at least one" are the same as the term "one or more" and can be employed interchangeably.

The term "about", as used in the context of the present invention, defines a range of +/−10%, preferably +/−5% of the specific value given.

All percentages given herein in relation to the compositions or formulations relate to weight % relative to the total weight of the respective composition or formula, if not explicitly stated otherwise.

The inventors have surprisingly found that the use of a hyper harmonized [$D_4$ ($\Phi/\phi$)] form of a hydroxyl modified fullerene (hereinafter referred to as "the hyper harmonized form") having a molecular formula of $C_{60}(OH)_xH_y\nabla_z$ (where x ranges from 24 to 48, or from 30-45; and y is from 0 to 24 and z is from 0 to 12) may be used instead of the previously disclosed harmonized form of the hydroxyl modified fullerene. The previously disclosed harmonized form of the hydroxyl modified fullerene is noted herein as [$D_3(\Phi/\varphi)$], where the oscillating magnetic field was applied according to:

$$D_3 = \begin{vmatrix} 3 & 5 & 8 \\ 13 & 21 & 34 \\ 55 & 89 & 144 \end{vmatrix} = 0$$

(hereinafter referred to as "$D_3$ rule").

The hyper harmonized [$D_4$ ($\Phi/\phi$)] form has hydrogen bonds that bond 2-3 times stronger than in ordinary water and 1.6 times stronger than the previously disclosed non-hyper harmonized [$D_3(\Phi/\varphi)$] form. A plurality of water layers may surround the hyper harmonized form of the hydroxyl modified fullerene, and the number of water layers may range from 4 water layers to 10 water layers, preferably 5 water layers to 10 water layers; whereas, the previously disclosed non-hyper harmonized form was disclosed to only have up to three water layers.

In addition, the hyper harmonized form of the hydroxyl modified fullerene may have an increased number of water molecules in the water layers as compared to the non-hyper harmonized form. For example, the hyper harmonized form may have or include from 12 water molecules independently to 6850 water molecules, preferably from 24 water molecules independently to 6000 water molecules, or more preferably from 40 water molecules independently to 5000 water molecules.

The hyper harmonized form may further have a remanent magnetism differing from a remanent magnetism of a non-harmonized $C_{60}(OH)_xH_y\nabla_z$ (where x is from 24 to 48, and y is from 0 to 24 and z is from 0 to 12) ranging from 2 nT to about 13 nT, preferably from 10 nT to 12 nT. The hyper harmonized form is contrasted to the non-hyper harmonized form, which had a potential remanent magnetism of 4 nT.

In addition, the hyper-harmonized form may have or include more water layers than the non-hyper harmonized form. The non-covalent O . . . H bonds of the hyper-harmonized form have a length that is about the same as that of the non-hyper harmonized form. However, the ability to have more water layers allows for hydrogen bonds between an oxygen a hydrogen that is farther away than 0.162 nm. For example, an oxygen may form a hydrogen bond with a hydrogen that has a length greater than 0.25 nm, preferably from 0.28 nm to 5 nm. Such hydrogen bonds are stronger than the hydrogen bonds in plain water and 1.6 times stronger than the hydrogen bonds present in the non-hyper harmonized form.

A method of preparing a hyper harmonized [$D_4$ ($\Phi/\phi$)] form of a hydroxyl modified fullerene having a molecular formula of $C_{60}(OH)_xH_y\nabla_z$ (where x is from 24 to 48, and y is from 0 to 24 and z is from 0 to 12) is also provided. The method may include adding a hydroxylated fullerene to ultra-pure water to form a mixture. The amount of the hydroxylated fullerene may be added to the ultra-pure water in an amount ranging from about 0.075 g/L to about 1 g/L based on the total volume of the mixture, preferably from about 0.15 g/L to about 0.75 g/L. Ultra-pure water is defined to mean water that has been purified according to very strict specifications to where the ultra-pure water only includes $H_2O$ molecules, $H^+$ ions, and $OH^-$ ions in equilibrium. Ultra-pure water is typically produced using membrane filtration, ion exchange, and the like as known to those skilled in the art. Ultra-pure water has an electrical resistance ranging from 16.8 MΩ to 18.6 MΩ, preferably with an electrical resistance of 18.2 MΩ.

The method may further include applying an oscillating magnetic field to the mixture at a temperature ranging from 34 C to 45 C, preferably from 36 to 38. The magnetic force of the oscillating magnetic field may range from 0.2 T to 1.8 T, preferably from 0.4 T to 1.2 T. The oscillating magnetic field may be applied to the mixture for a period of time ranging from 54 minutes to 90 minutes, preferably from 72 minutes to 81 minutes. "Oscillating magnetic field" may preferably be an alternating oscillator field for purposes of the present invention described herein.

In various embodiments, the oscillating magnetic field is applied for a period of time ranging from 54 minutes to 90 minutes, preferably from 72 minutes to 81 minutes. The period of time may be divided into 6 sessions where a first session of the oscillating magnetic field is applied at +0.5 T according to:

$$D_4 = \begin{vmatrix} 1 & 2 & 3 & 5 \\ 8 & 13 & 21 & 34 \\ 55 & 89 & 144 & 233 \\ 377 & 610 & 987 & 1597 \end{vmatrix} = 0$$

(hereinafter referred to as "$D_4$ rule").

A second session of the oscillating magnetic field is applied at −0.5 T; a third session of the oscillating magnetic field is applied at +0.5 T; a fourth session of the oscillating magnetic field is applied at −0.5 T; a fifth session of the oscillating magnetic field is applied at +0.5 T; a sixth session of the oscillating magnetic field is applied at −0.5 T. For example, the period of time may be 54 minutes, and each session may be 9 minutes each. In alternative embodiments, one or more sessions may have a different period of time than a preceding session.

After the oscillating magnetic field is applied to the mixture, a composition is formed where the composition includes a hyper harmonized form of a hydroxyl modified fullerene having a plurality of water layers surrounding the hyper harmonized form of the hydroxyl modified fullerene. The plurality of water layers may have or include from 4 water layers to 10 water layers, preferably from 5 water layers to 9 water layers. The substance may have a diameter ranging from 6 nm to 15 nm, such as 14.5 nm; the diameter indicates the number of water layers present.

The forming of the composition may optionally include additional components, such as fluorescent tags, dyes, fillers, or other components known to those skilled in the art.

FIG. 1 a shows a Co fullerene 10 composed entirely of carbon atoms in the form of a hollow sphere in the shape of the familiar black and white soccer ball (Telestar 1970). Fullerenes comprise a family of carbon allotropes containing from 20 to 1000 or more carbon atoms in each cage-like structure. The structure of Co fullerene is a truncated icosahedron having 20 hexagon faces 12, 12 pentagon faces 14, all single bonds along pentagon perimeters 16, one double bond 18 and 2 single bonds per carbon. The Co has two bond lengths. A first bond length is along the edges of two hexagons and the second bond length is between the edge of a hexagon and a pentagon, the first bond length being greater than the second bond length. One of the crucial properties of the fullerene Co is the energy states of $T_{1g}$, $T_{2g}$, $T_{1u}$ and $T_{2u}$ for symmetry elements $C_5$, $C_5^2$, $S_{10}$ and $S_{10}^3$ are consistent with the golden mean. (Koruga, et. al., 1993, Dreselhaus, et al., 1996). Since, the symmetry properties of the structure is determinate of its vibration and rotation energy states, it has been shown that integral energy (translational, vibrational, rotational and electronic) states of fallerene Co follows the golden mean rule or ratio (Harter, 1989).

FIG. 2 shows a figural representation 21 of the golden mean rule or golden ratio. The golden ratio usually designated with the symbol Φ and expresses the relationship that the sum of two quantities is to the larger quantify as the larger quantify is to the smaller quantity, that is a+b is to a as a is to b. The golden ratio can be expressed mathematically as:

$$\Phi = \pm(1+\sqrt{5})/2 \approx \pm1.618033$$

The conjugate golden ratio φ=±1/Φ≈±0.618 corresponds to the length ratio taken in reverse order b/a.

In a preferred form of the invention, FIG. 1 b shows fullerenes modified 20 with multiple hydroxyl groups (OH)x 26, multiple hydrogen atoms (Hy), and/or molecules with one or more molecules with hydroxyl groups ∀z to form substances C60 (OH)xHy∀z (where x is from 10 to 36, and y from 0 to 24 and z from 0 to 12). These compounds will be referred to herein as modified fullerenes 20. Modified fullerenes are soluble in water and interact with water via hydrogen bonds. Modified fullerenes are susceptible to degradation from environmental and chemical attacks. Such exposure to environmental and chemical agents can lead to a removal of functional groups from the Modified Fullerene. This is undesirable as unmodified or "naked" fullerenes C60 have been found to be cytotoxic.

Experiments with $C_{60}(OH)_{24}$ 20 (FIG. 1 b) in two different human cell lines show that the cytotoxicity is a sensitive function of surface derivatization (Sayes, 2004). Experiments strongly suggest that the mechanism of cell death is oxygen radical induced peroxidation of the lipid bilayers of cells by "naked" nano-$C_{60}$. In experiment with human dermal fibroblasts, human liver carcinoma cells (HepG2), and neuronal human astrocytes at doses higher than 50 ppb ($LC_{50}$=2-50 ppb, depending on cell type) cytotoxicity arise after 48 h of exposure (Sayes, 2004). However, in the same experiments it was shown modified fullerenes 20, show no cytotoxicity. Thus, it is an important aspect of the present invention to provide a stable Modified Fullerene.

Toxicity test for harmonized, modified fullerenes has shown this substance is not cytotoxic when the material is subjected to a *Salmonella typhimurium* reverse mutation assay (AMES test). The Ames test is used to determine any potential mutagenic activity of the test HHMF material. The HHMF material was exposed to a large number of test organism in an agar plate. The agar plates were monitored for growth of revertants (organisms mutating to the wild type). The number of wild type organisms are counted to estimate the mutagenic potential of the HHMF material. The tests results showed the HHMF material was not mutagenic.

It has been found by the present inventor, the modified fullerenes can be stabilized in a harmonization process. Modified Fullerenes, are made by a procedure described in U.S. Pat. No. 5,648,523 which is incorporated herein by reference in its entirety by reference and made a part hereof. More particularly, modified fullerenes can be prepared by one of the following six methods. First, Modified Fullerene can be prepared from hydrolysis of the reaction products of fullerenes, either pure $C_{60}$ or a mixture of $C_{60}$ (84%) and $C_{70}$ (16%), with nitronium tetrafluoroborate in the presence of organocarboxylic acid ($RCO_2H$) at ambient temperature. Chiang, et al., U.S. Pat. No. 5,177,248; et al. U.S. Pat. No. 5,294,732; and et al., J. Am. Chem. Soc. 1992, 114, 10154; Chiang, et al., J. Am. Chem. Soc. 1993, 115, 5453. The structure of the resultant Modified Fullerene has been characterized to consist of $C_{60}O_x$ $(OH)_y$ with x<5 and y=18 on average.

Second, a Modified Fullerene can be synthesized via hydrolysis of the reaction products of fullerenes, either pure Co or a mixture of $C_{60}$ (85%) and $C_{70}$ (16%), with a solution of sulfur trioxide (30%) in sulfuric acid. See Chiang, et al., J. Org. Chem. 1994, 59, 3960. The structure of the resultant Modified Fullerene has been characterized to consist of $C_{60}$ $(OH)_y$ with y=12 on average.

Third, a modified Fullerene can be prepared by the reaction of fullerenes with either a mixture of conc. $H_2SO_4$, conc. $HNO_3$ and water at 90° C. or a mixture of oleum ($H_2SO_4$—$SO_3$), $KNO_2$ and water. See Chiang, et al., U.S. Pat. Nos. 5,177,248; 5,294,732; J. Chem. Soc., Chem. Commun. 1992, 1791; Chiang, et al., Mat. Res. Soc. Symp. Proc. 1992, 247. The structure of the resultant Modified Fullerene has been characterized to consist of $C_{60}O_x$ $(OH)_y$ with x<5 and y=15 on average.

Fourth, a Modified Fullerene can be synthesized by the reaction of fullerenes, dissolved in either benzene or toluene, with aqueous sodium hydroxide in the presence of a catalytic amount of tetrabutylammonium hydroxide and oxygen (in air). See Li, et al., J. Chem. Soc., Chem. Commun. 1993, 1784. The structure of the resultant Modified Fullerene has been characterized to consist of polyhydroxylated Co fullerene derivatives with 26 hydroxy groups per $C_{60}$ cage on average.

Fifth, a Modified Fullerene can be prepared by the reaction of fullerenes, dissolved in either benzene or toluene, and gaseous nitrogen dioxide, followed by hydrolysis of resulting products with aqueous NaOH. See Chiang, et al., Tetrahedron, "Efficient Own-Flask Synthesis of Water-soluble Fullerenols." Gaseous nitrogen dioxide can be generated by either reacting $NaNO_2$ with $FeSO_4$ in aqueous $H_2SO_4$ in the presence of air (Roy, et al., J. Chem. Soc., Chem. Commun. 1994, 275) or reacting $NaNO_2$ with conc. $HNO_3$. The former method yields nitrofullerenols consisting of 6-8 nitro and 7-12 hydroxyl groups per Co. Hydrolysis of these products results in modified fullerenes with 13-20 hydroxy groups per $C_{60}$. The later method gives water-soluble modified fullerenes with a maximum number of hydroxyl groups per $C_{60}$ as 20 as identified by the FAB mass spectroscopy.

Sixth, a Modified Fullerene can be synthesized by the reaction of fullerenes with an excess of $BH_3$-tetrahydrofuran (THF) complex followed by hydrolysis with either sodium hydroxide/hydrogen peroxide or sodium hydroxide. See Schneider, et al., J. Chem. Soc., Chem. Commun. 1994, 463.

Harmonizing the Modified Fullerene

To stabilize the modified fullerenes to withstand chemical and environmental attacks to avoid stripping of their functional groups, the modified fullerenes are subjected to a harmonization procedure. The harmonization procedure promotes the electron energy levels of the molecular orbitals of the O13 H covalent bonds from a ground state (FIG. 6 a) up one energy level to a harmonized state (FIG. 6 c) where the valence electrons 50 are at a greater distance away from the nucleus than when in the ground state. This creates larger distances between bonding sites on the spherical surface of the Modified Fullerene of hydrogen electrons of x and y groups, forming a dynamical, non-localized cloud "θ cloud" 84 (FIG. 9) of electrons capable of forming a hydrogen bonding network. In one preferred form of the invention, energy state of the θ cloud assumes the shape of a "sunflower" pattern 52.

FIGS. 6 a-c shows the electron cloud of a hydrogen atom in three different states. FIG. 6 a shows the electron cloud in a ground, unexcited, state. FIG. 6 b shows the same electron cloud when exposed to random radiation showing the electrons in an excited state resulting with a substantial portion of the electrons in positions farther from the nucleus when compared to the electrons in the ground state. FIG. 6 c shows the electron cloud of hydrogen atoms exposed to harmonized excitation energy ($E^{\Phi/\Phi}$) as opposed to random radiation. The sunflower shaped θ cloud 84 allows for hydrogen atoms to hydrogen bond to oxygen atom wherein the hydrogen bond the length of the O—H covalent bond and the length of the H—O . . . H hydrogen bond length obey the golden ratio shown in FIGS. 2 and 5 and described above.

Prior to 1999, the standard teaching stated that hydrogen bonds existed between water molecules because of the electrical attractions between a positively charged hydrogen atom and a negatively charged oxygen atom in a neighboring molecule. These electrostatic interactions can be explained perfectly by classical physics—Coulomb's law, by which it is possible to describe the attraction and repulsion between charged particles separated from each other by a distance. Experiments carried out in 1999 clearly showed that electrons, like all other objects in nature, naturally seek their lowest energy state, through minimization of their total energy (including their energy of motion). Lowering an electron's kinetic energy means reducing its velocity and momentum. According to the Heisenberg Uncertainty Principle, by reducing the momentum of electrons the electrons must spread out in space thereby delocalizing the electrons into a semi-π electron cloud 84 (θ cloud). In other words, the electrons in the hydrogen bond are quantum mechanically shared with more than one bonding site. Isaacs' experiment provides unambiguous evidence of the possible existence of multi-bonding hydrogen electrons in hydrogen bonds. Recent studies of hydrogen bonding in water, using very fast multi-dimensional nonlinear infrared spectroscopy, shows that hydrogen-bonded network of liquid water has an energy redistribution on a femtosecond timescale (Cowan, 2005). Those experiments prove that multi-bonding hydrogen electrons exist and play an important role in hydrogen bond network of matter.

The hydrogen atom is the simplest case of positive/negative charge organization in a spherical shape because it has a nucleus of one proton and one electron orbiting the nucleus. The electron has a certain total energy; the essence of quantum theory is that electrons remain in stable states of specific energies, and for each state there is a particular orbit. When an electron is in the lowest energy level, called the ground state, its Bohr radius is 52.9 pm. The electron must gain energy to move out to larger orbits. The orbits, and so the energy levels, follow strict spacing rules determined by quantum physics. Energy can be added to the atom either by collision with another particle or by absorption of a photon with sufficient energy. When the electron jumps up one or more energy levels the hydrogen is said to be in an excited state with an orbital radius of 236.8 pm for level two and 473.0 pm for level three (Lyman series). In normal conditions, electrons remain in an excited state for a very short period of time and drop to a lower level in about $10^{-8}$ seconds (Balmar series), emitting a photon with energy equal to the difference in the energy of the excited level to the level to which it drops. A hydrogen atom is in state one (ground state) as a gas $H_2$ or in an inorganic compound. However, hydrogen atoms in biomolecules and biological water are mostly in state two. Hydrogen ions in water have a quasi-proton existence because the proton never exists in aqueous solution as a free ion; it is always hydrated by being associated with neighboring water molecules. A proton in aqueous solution is very mobile, hopping from one water molecule to another with a period of about $10^{-15}$ second.

The potential importance of hydrogen bonding in the structure and function of biomolecules was predicted by Pauling and Corey (1951), Watson and Crick (1953) and numerous other scientists. Hydrogen bond energies can vary in strength depending on numerous factors and can have values of 15-40 kcal/mol, 4-15 kcal/mol and 1-4 kcal/mol for strong bonds, moderate bonds and weak bonds, respectively. Intermolecular hydrogen bonds have a force constant ranging from 60 N/m to 120 N/m. In a preferred form of the present invention, hydrogen bonds will be of moderate strength with a force constant of about 80 N/m and energies 4-15 kcal/mol. Such moderate hydrogen bond strengths correspond to a hydrogen bonding structure having a distance from a center of a donor atom to a center of an acceptor atom of about 280±10 pm.

It is well known that hydrogen-bonding 32 exists in functional groups 33 in protein side chains 34 (See FIG. 3 *a*, healthy hydrogen bonding) such as in: lysine-histidine or tryptophan, arginine-glutamic acid or asparagic acid, tryptophan or praline, or histidine-tyrosine or threonine or serine in a donor-acceptor interaction. In protein and nucleic acid structures the distance from the center of a donor atom to the center of an acceptor atom is 290±10 pm and 310±20 pm, respectively. However, this intramolecular hydrogen bonding in functional groups of proteins is dynamic in nature with neighboring water molecules "competing" to take a donor or acceptor position normally occupied by an atom in the protein. In some cases, under the influence of external or internal factors, a water molecule 37 may occupy the position of a natural, intramolecular, hydrogen bond 38 in proteins (FIG. 3 *b*, unhealthy hydrogen bonding), changing the conformation of the protein and its functional characteristics.

Figures 3, 4, 5:
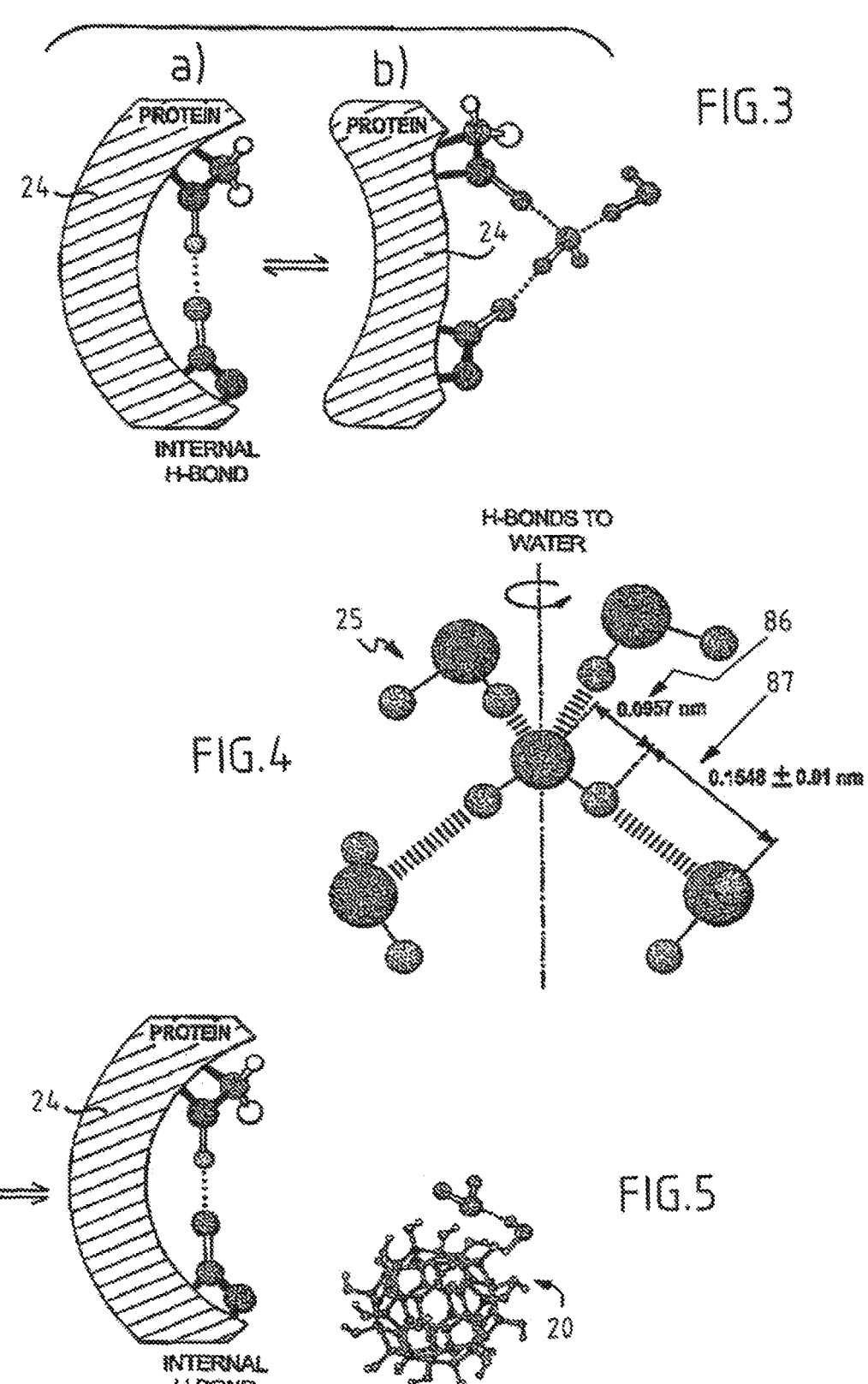
FIG. 4 is a diagram of a cluster of water molecules showing that the ratio of the length of an O—H covalent bond to the length of a hydrogen bond obeys the golden ratio.
FIG. 5 is a diagrammatic view of a hydroxyl-modified fullerene scavenging a water molecule to return the protein 24 to a healthy state shown in FIG. 3*a*.

We have identified a direct correlation between the energy levels of the unhealthy hydrogen bonding to the structural intramolecular integrity of biomolecules (e.g., protein, DNA, among others). We further identified that a biomolecule (e.g., protein, DNA, among others) is "healthy" (FIG. 3 *a*) (i.e., having normal and natural functionality with constituent molecules at the intrinsic global energy level possible for that biomolecule) when water molecules interact and are connected to the biomolecules via weak bonds. In this healthy state the biomolecule operates at its optimal and most efficient state, maximizing proper functional interaction with other biomolecules (e.g., between different procollagen biomolecules which gives collagen fibers its structure) and efficient interaction with the molecular system as a whole. We have also observed that biomolecules, that are healthy, have a different structural confirmation state from that observed in "unhealthy" biomolecules (FIG. 3 *b*). Additionally, we discovered that through external influence, a non-healthy biomolecule can adopt the structural confirmation of that observed in a healthy biomolecule (FIG. 4). This structural confirmation state change, in-turn, helps attract and develop non-covalent bonds with adjacent water molecule(s) and adjacent hydroxyl group(s) (OH), helping the previously "unhealthy" biomolecule to return to good health. This confirmation change for unhealthy biomolecules can be achieved by exposing the unhealthy biomolecule to an externally induced excitation frequency with a wave number between 500 to 3800 cm$^{-1}$, a wavelength ranging from 2.63 to 20 μm, or an energy ranging from 0.06 eV to 0.47 eV.

One suitable source of the externally induced excitation energy having a wave number between 500 to 3800 cm$^{-1}$ can be provided by exposure of the unhealthy biomolecule to a harmonized Modified Fullerene 20 as shown in FIGS. 4 and 9. The harmonized Modified Fullerene 20 influences and enables the unhealthy biomolecule to attract and develop a non-covalent bond with adjacent water molecule(s) and adjacent hydroxyl group(s) (OH). This leads to the biomolecule "self-repairing" itself and returning to good "health" leading to beneficial health outcomes. The energy state (T1 g, T2g, T1u and T2u) of the harmonized Modified Fullerene product provides the necessary excitation frequency with a wave number from 500 to 3800 cm−1.

The harmonization procedure requires forming a solution of the Modified Fullerenes and exposing the solution to polarized light, heating and a pulsing magnetic field. More particularly, solutions of Modified Fullerene are formed by dissolving the Modified Fullerene into an aqueous solution or other solubilizing agent. These solutions are optionally subjected to ultrasonication for 10 to 30 minutes. The Modified Fullerene-containing solution is then treated by exposure for a period of 0.5 hours to 2 hours simultaneously to: (1) a pulsing polarized light where the power source pulses from 20 W to 500 W in accordance with the (Fibonacci series "φ"), from a distance of 10 cm to 60 cm, and with a wave length of 320 nm to 4200 nm; (2) heating the solution while continuously stirring from 20° C. to 80° C. for ⅓ of the treatment time period followed by cooling the solution from 80° C. to 15° C. for ⅔ of the treatment time period; and (3) subjecting the solution to an oscillatory (Fibonacci series "Φ") magnetic field intensity from 0.4 T to 1.2 T. This procedure can be conducted in a "PHM system" (Photo-Heath-Magnet Devices) where solutions of volumes from 0.2-3 liters can be treated.

According to this procedure, the θ cloud 84 of temporally delocalized electrons of the hydrogen bonds of the now harmonized Modified Fullerene move around the surface of the harmonized Modified Fullerene forming a magnetic shield 84 (FIG. 9) (nano-magnetosphere) having an intensity from 0.5 nT to 25 nT, the intensity oscillating in accordance with the golden mean law. If some molecules with positive or negative charges try to "attack" the harmonized Modified Fullerene they will glide behind the nano-magnetosphere, somewhat like how charged particles from outer space glide over the Earth's magnetosphere. Because the entire surface of the harmonized Modified Fullerene is enveloped in a Θ cloud 84 means that when viewed from the outside the harmonized Modified Fullerene will appear as one body mass with equal mass distribution in space.

We characterized the starting Modified Fullerene and the harmonized Modified Fullerene ($[C_{60}(OH)_{10-36}]^{\Phi/\varphi}$) as follows: (1) starting substance $C_{60}(OH)_{10-36}$ with NMR ($^1$H NMR Bruker AC 250 E, 250 MHz and $^{13}$C NMR 62.9 MHz), IR (Perkin Elmer 457, FTIR Bomem MB100 FT), UV/Vis Perkin-Elmer series λ, ESR (Bruker ESR-300), TG (DuPont 1090 TA, TGA 951) and remanent magnetism (JR-5, with accuracy±3 pT), (2) after harmonization [$C_{60}$ $(OH)_{10-36}]^{\Phi/\varphi}$ with $^{13}$C NMR and JR-5, (3) collagen in vitro with IR and FTIR before and after the harmonization procedure, (4) group of 50 mice which were induced by carcinoma before and after influence [$C_{60}(OH)_{10-36}]^{\Phi/\varphi}$, (5) group of 60 people with different skin problems including wrinkle, rashes, pigmentation, BCC, and skin cancer with documentation which include clinical pictures before and after treatment by [$C_{60}(OH)_{10-36}]^{\Phi/\varphi}$, and (6) six human skin biopsies with characterization state of epiderm, basal membrane, collagen and elastin before and after treatment by [$C_{60}(OH)_{10-36}]^{\Phi/\varphi}$.

NMR is an effective characterization technique to distinguish a harmonized form of [$C_{60}(OH)_{10-36}]^{\Phi/\varphi}$ from a nonharmonized form $C_{60}(OH)_{10-36}$. A non-harmonized form of $C_{60}(OH)_{10-36}$ will have a dominant peak from 72 ppm to 78 ppm representing the $C_{60}(OH)_{10-36}$ functional body (FIG. 7). Smaller peaks flank the dominant peak from 65.0 ppm to 95.0 ppm indicating that each atom of the $C_{60}$ is not equally covered by OH groups. The peak at 92.5 ppm indicates the presence of a catalysts such as NaBr, NaOH and $D_2O$. A small peak at 143.0 ppm indicates the presence of pure $C_{60}$ (C=C bonds).

FIG. 7 is a $^{13}$C NMR spectra 100 for $C_{60}(OH)_{24}$. A dominant peak 102 is located at 77.5 ppm flanked on both downfield and upfield sides by numerous smaller peaks, collectively referred to as 104, from 65 ppm to about 90 ppm. The dominant peak 102 represents the chemical shift ($\delta$) 77.5 ppm indicating a $C_{60}OH_{24}$ functional body. The numerous smaller peaks are from 65 ppm to about 90 ppm are representative of the $C_{60}OH$ functional group(s). Thus, it is clear that not all Co are equally surrounded by OH groups.

FIG. 8 shows a $^{13}$C NMR spectra for a harmonized, hydroxyl modified fullerene $[C_{60}(OH)_{24}]^{\Phi/\phi}$ 200 having a single dominant peak 202 at 170.2 ppm which indicates that each carbon atom of $C_{60}$ is equally covered by OH groups (notwithstanding the number of carbon atoms is 60, while number of OH groups is 24). Harmonized hydroxyl modified fullerene substance "appears" as a one body system. Peaks with smaller intensity on 77.5 ppm and 143.0 ppm indicate the presence of a small amount of non-harmonized hydroxyl modified fullerene substance and pure $C_{60}$ fullerenes, respectively. Thus, the harmonized, hydroxyl-modified fullerene shows all functional groups resonate at the same frequency, and, therefore appear as a body which has equal mass distribution in space.

The remanent magnetism of $C_{60}(OH)_{24}$ was measured before and after subjecting the $C_{60}(OH)_{24}$ to a harmonization procedure described above. The harmonized, hydroxyl modified fullerene $[C_{60}(OH)_{24}]^{\Phi/\phi}$ showed an increased magnetic field strength of about 4 nT.

Hydrated Harmonized Modified Fullerenes

FIG. 9 shows a harmonized Modified Fullerene 20 surrounded by water molecules 37 (hydrated harmonized Modified Fullerene). Three levels of hydrogen bonding are shown. The first level of hydrogen bonding 60 is between a hydrogen atom 62 of an OH group 26 and an oxygen atom 64 of an adjacent OH group 26 with each of these OH groups 26 covalently bonded to a carbon atom of the harmonized Modified Fullerene 20.

A second level of hydrogen bonding 70 occurs between an oxygen atom 64 of an OH group 26 of the harmonized Modified Fullerene 20 and a hydrogen atom 72 of a water molecule 37. The effects of the $\theta$ cloud 84 of temporally delocalized electrons of the harmonized Modified Fullerene acts as a template to cause the hydrogen bond lengths 70 between the harmonized Modified Fullerene 20 and the water molecules directly hydrogen bonding thereto, to obey the Fibonacci law. FIG. 4 shows a cluster of water molecules 25 having a covalent bond length 86 of 0.0957 nm and a hydrogen bond length 87 of 0.1548 nm wherein a ratio of the hydrogen bond length to the covalent bond length is 0.1548/0.0957=1.6175 which is 99.97% of the golden ratio of 1.61803. The intermolecular formula for this hydrated form of the harmonized Modified Fullerene will be designated as $[C_{60}(OH)_{24}]^{(\Phi/\phi)}\cdot n(H_2O)$.

A third level of hydrogen bonding 80 occurs between hydrogen atoms 72 of water molecules 37 and oxygen atoms 82 of adjacent water molecules 72. The intermolecular formula for this two-layered hydrated structure will be designated as $\{[C_{60}(OH)_{24}]^{(\Phi/\phi)}\cdot n(H_2O)\}m(H_2O)$.

The first level of hydrogen bonds is the strongest of the three and is 1.8 times stronger than the level three hydrogen bonds 80. The second level of hydrogen bonds 70 is the second strongest of the three levels and has a strength of 1.5 times that of level three hydrogen bonds 80. The hydrogen bonds of levels one and two provide the electron cloud 84 and produce an oscillatory magnetic field of 0.5 nT and causes water molecule surrounding the harmonized Modified Fullerene 20 to generate a magnetic field up to 4 nT.

A third hydrated form of the harmonized Modified Fullerene will include ions and will have the intermolecular formula of $\{[C_{60}(OH)_{24\text{-}48}]^{(\Phi/\phi)}\cdot n(H_2O)\cdot p(Na^+, Cl^-, Mg^{2+}, Ca^{2+}, \text{and other ions})\cdot m(H_2O)$. The ions can be present in an amount by weight ranging from about 0.01% to about 10%, preferably from about 0.1% to about 5%, more preferably from about 0.5% to about 1%.

Cosmetic Products Based on $D_4[C_{60}(OH)_{24\text{-}48}]^{\Phi/\phi}$

Cosmetic products containing the hyper harmonized Modified Fullerene (HHMF) can include from 10 to 30% by weight, more preferably from 12-20% and most preferably from 0.5-8% of the HHMF with other substances commonly used in cosmetics to produce cosmetic compounds; moisturizing lotions, gels and oils; sun protection lotion, gels and oils; and other cosmetic products. Suitable delivery vehicles or components of such cosmetics can include, but are not limited to aqua purificate, propylene glycol, isopropyl isostearate, caprylic/capric triglyceride, *Butyrospermum parkii* (Shea Butter), C12-20 acid PEG-8 ester, butyl methoxydibenzoylmethane, squalane, DEA-cetil phosphate, carbomer, *Simmondsia chinensis* (Jojoba) seed oil, *echinacea angustifolia* extract, parfum, phenoxyethanol, methylparaben, propylparaben, ethylparaben, butylparaben, isobutylparaben, PEG-8, tocopherol, ascorbyl palmitate, ascorbic acid, citric acid, hydrolyzed serum protein, hydrolized yeast protein, pyridoxine, niacinamide, panthenol, allantoin, biotin, Vitamin C, sodium sydrocside, sodium, potassium, magnesium, zinc, cobalt, iron, chloride/sulfate, pentylene glycol, glycerin, propylene glycol, carbomer, sodium hydroxide, coenzyme Q10, vitamin A, vitamin E, proline, silver nanoparticulate, gold nanoparticulate, zinc oxide nanoparticulate, titanium dioxide nanoparticulate, active carbon micro- and nanoparticulate, and any type of icosohedral fullerenes.

The hyper harmonized form cosmetic products are useful for numerous skin treatments including but not limited to, skin cancer, melanoma, non-melanoma, basal cell carcinoma, squamous cell carcinoma, merkle cell carcinoma, Bowen's disease, eccrine porocarcinoma, actinic keratosis, seborrheic keratosis, actinic porokeratosis, wounds, scars, inflammations, acne, rosacea, eczema, hyper-pigmentation, anti-aging prevention, wrinkle reduction, herpes, rashes, pimples, boils, sun-damage, solar lentigo, skin conditioning, skin rejuvenation, oily skin, stretch marks, cold sores, vein ulcers, incision scar healing, and other skin damage repairs, or conditions.

Example 1

In FIGS. 10A-10D, ultraviolet (UV) light measurements were taken on bare skin (FIG. 10A), skin after a cream base was applied (FIG. 10B), skin after a classical cream was applied (FIG. 10C), and skin after a cream with the hyper harmonized form of the hydroxyl modified fullerene was applied (FIG. 10D). In each case, the measurements were taken after the cream was applied to an inner forearm of a In each situation, the cream was applied to a thickness of 80-150 micrometers on a human's forearm; the cream was applied in one drop that was 280 mg on an area of 16 cm$^2$. The cream base used in the graph of FIG. 10B was ZEPUR PNK-242 supplied by Zepter Cosmetics produced in Intercosmetica, Switzerland. The classical cream of FIG. 10C was ZEPUR 242$^{++}$ supplied by also supplied by Zepter Cosmetics produced in Intercosmetica, Switzerland. The cream used in conjunction with the hyper harmonized hydroxyl modified fullerene of FIG. 10D was ZEPUR 242$^{++}$ supplied by Zepter Cosmetics produced in Intercosmetica, Switzerland; the hyper harmonized hydroxyl modified fullerene was present in the cream in an amount of 12% by weight based on the total composition.

The measurements were taken 20 minutes after the noted treatment was applied in each graph. A UV/VIS/NIR spectrometer from Hamamatsu, Japan was used to take the measurements.

As noted in FIG. 10D, the peak shifts from 380 nm (in FIGS. 10A-10C) to 390 nm (in FIG. 10D). This signifies that the skin appears slightly whiter because of a biophysical phenomenon based on the inclusion of the hyper harmonized form of the hydroxyl modified fullerene in the cream. The peak shift also indicates that the appearance of the skin to be slightly whiter is not due to a melanin increase or other biochemical reason.

Example 2

In FIGS. 11A-11B, measurements were taken before and after a treatment where a cream having the hyper harmonized form of the hydroxyl modified fullerene was applied to a hand. The measurements were performed with an OMIS device that does opto/magnetic imaging spectroscopy. The y-axis is noted as "P+/P−", which indicates a value of paired (P+) and unpaired (P−) electrons in the tissue before and after treatment. FIG. 11A represents a ratio of paired and unpaired electrons in the basal membrane using UV light with a peak on 370 nm. FIG. 11A illustrates that the peak shifts to the visible spectrum when the treatment is applied to the skin.

In each situation, the cream was applied to a thickness of 120-180 micrometers on a the hand of a person; the cream was applied in one drop that was 280 mg on an area of 16 cm$^2$. The hand cream used in the graph of FIG. 11A was ZEPUR 242$^{++}$ supplied by Zepter Cosmetics produced in Intercosmetica, Switzerland. The hand cream used in the graph of FIG. 11B was ZEPUR 242$^{++}$ supplied by Zepter Cosmetics produced in Intercosmetica, Switzerland.

The measurements were taken 20 minutes after the treatment was applied in each graph. The measurements were performed with an OMIS device that does opto/magnetic imaging spectroscopy.

As noted in FIGS. 11A-11B, the ratio of paired and unpaired electrons (P+/P−) drops to about 0.5 after the treatment. This indicates that the tissue is a dynamic complex system where unpaired and paired electrons play an important role. If there are more unpaired electrons present in the tissue, the tissue is paramagnetic; whereas, if there are more paired electrons in the tissue, the tissue is diamagnetic. For tissue, the best ratio is from 0.4 to 0.6 for paired to unpaired electrons, which indicates that the basal membrane is improved if the ratio is higher than 0.6 and then falls within this range after treatment. In FIG. 11A, the ratio started at about 0.62 and improved to a ratio of about 0.49. In FIG. 11B, the ratio was about 0.79 and improved to a ratio of about 0.52.

FIG. 12 illustrates a hyper harmonized hydroxyl modified fullerene and how it functions in its environment. The fullerene 1 can be a C$_{60}$ molecule or any other higher fullerene molecule having icosahedral symmetry or dodecahedral symmetry. The OH groups 2 are covalently linked with the fullerene 1. The water layers 3 may form hydrogen bonds, such as those described above, that are generated by the oscillatory magnetic field D4 (Φ/φ); there may be from 3 to 10 water layers. The water environment 4 surrounds the water layers 3, and the water environment 4 may form weaker hydrogen bonds with the water layers 3 as compared to the hydrogen bonds between the water layers 3 and the OH groups 2.

Example 3

A tomato plant was treated with the hyper harmonized form of the hydroxyl modified fullerene and tested under different types of light to determine the amount of lycopene under various conditions.

In the first aspect of the experiment, the lycopene was measured for a control tomato plant where only diffuse light was applied, and the lycopene was measured for a tomato plant where the treatment was applied in addition to the diffuse light. The treatment consisted of watering the tomato plants every third day with 50 mL of water per 1 kg of soil, and the concentration of the treatment was 0.075 g/L of the hyper harmonized form of the hydroxylated modified fullerene. The control tomato plant had a lycopene concentration of 145.9±0.51 mg/kg. The treated tomato plant had a lycopene concentration of 210.7±0.57 mg/kg, which was an increase of 65 mg/kg due to the hyper harmonized form of the treatment.

In the second aspect of the experiment, the lycopene was measured for a control tomato plant where only hyperpolarized light (HPL) was applied, and the lycopene was measured for a tomato plant where the treatment was applied in addition to the HPL. The treatment consisted of watering the tomato plants every third day with 50 mL of water per 1 kg of soil, and the concentration of the treatment was 0.075 g/L of the hyper harmonized form of the hydroxylated modified fullerene. The control tomato plant had a lycopene concentration of 323.8±0.45 mg/kg. The treated tomato plant had a lycopene concentration of 395.9±0.34 mg/kg, which was an increase of 72 mg/kg due to the hyper harmonized form of the treatment.

In the third aspect of the experiment, the lycopene was measured for a control tomato plant where only linearpolarized light (LPL) was applied, and the lycopene was measured for a tomato plant where the treatment was applied in addition to the LPL. The treatment consisted of watering the tomato plants every third day with 50 mL of water per 1 kg of soil, and the concentration of the treatment was 0.075 g/L of the hyper harmonized form of the hydroxylated modified fullerene. The control tomato plant had a lycopene concentration of 222.4±0.34 mg/kg. The treated tomato plant had a lycopene concentration of 366.2±0.44 mg/kg, which was an increase of 144 mg/kg due to the hyper harmonized form of the treatment.

Thus, treating the tomato plant with the hyper harmonized form of the hydroxyl modified fullerene significantly increased the lycopene content of the tomato plant.

From the foregoing it will be observed that numerous variations and modifications may be effected without departing from the spirit and scope of the invention. It is to be understood that no limitation with respect to the specific inventions disclosed herein is intended or should be inferred. It is, of course, intended to cover by the appended claims all such modifications as fall within the scope of the claims.

The invention claimed is:

1. A composition comprising:

a hyper harmonized ([D4 (Φ/φ)]) form of a hydroxyl modified fullerene having a molecular formula of C$_{60}$(OH)$_x$H$_y$∀$_z$, where x is from 24 to 48, and y is from 0 to 24 and z is from 0 to 12; and a plurality of water layers surrounding the hyper harmonized form of the hydroxyl modified fullerene; wherein the plurality of water layers comprises from 4 water layers to 10 water layers, wherein the composition has a remanent magnetism differing from a remanent magnetism of a non-harmonized $C_{60}(OH)_x H_y \forall_z$, where x is from 24 to 48, and y is from 0 to 24 and z is from 0 to 12, ranging from 10 nT to 12 nT.

2. The composition of claim 1, wherein an amount of water molecules within the plurality of water layers ranges from 12 water molecules to about 6850 water molecules.

3. The composition of claim 1, wherein the molecular formula is $[C_{60}(OH)_x]^{[D4\ (\Phi/\phi)]}$ where x is from 24 to 48.

4. The composition of claim 1, wherein a length of one or more hydrogen bonds is greater than 0.25 nm.

5. The composition of claim 1, wherein an intermolecular formula is $\{[C_{60}(OH)_x]^{[D4\ (\Phi/\phi)]}\cdot n(H_2O)\}\cdot p$ (at least one of $Na^+$, $Cl^-$, $Mg^{2+}$, and $Ca^{2+}$) where x is from 24 to 48, where n is the number of water molecules and p is the number of ions and wherein the n-water molecules are arranged within the plurality of water layers, and p-ions are present in an amount by weight relative to the total weight of the intermolecular formula ranging from 0.01% to 10%.

6. The composition of claim 1, wherein an intermolecular formula is $\{[C_{60}(OH)_x]^{[D4\ (\Phi/\phi)]}\cdot n(H_2O)\cdot p$ (at least one of $Na^+$, $Cl^-$, $Mg^{2+}$, and $Ca^{2+})\cdot m(H_2O)\}$, where n and m are the number of water molecules and p is the number of ions.

7. The composition of claim 1 is not cytotoxic when measured by an Ames test.

8. The composition of claim 1, further comprising a carrier selected from the group consisting of aqua purificate, propylene glycol, isopropyl isostearate, caprylic/capric triglyceride, *Butyrospermum parkii* (Shea Butter), C12-20 acid PEG-8 ester, butyl methoxydibenzoylmethane, squalane, DEA-cetil phosphate, carbomer, *Simmondsia chinensis* (Jojoba) seed oil, *Echinacea angustifolia* extract, parfum, phenoxyethanol, methylparaben, propylparaben, ethylparaben, butylparaben, isobutylparaben, PEG-8, tocopherol, ascorbyl palmitate, ascorbic acid, citric acid, hydrolyzed serum protein, hydrolized yeast protein, pyridoxine, niacinamide, panthenol, allantoin, biotin, Vitamin C, Vitamin E, Vitamin A, sodium sydrocside, sodium, potassium, magnesium, zinc, cobalt, iron, chloride/sulfate, pentylene glycol, glycerin, propylene glycol, carbomer, and sodium hydroxide.

9. The composition of claim 8, further comprising a therapeutic substance.

10. The composition of claim 9, wherein the therapeutic substance is selected from the group consisting of vitamins, hormones, peptides, polypeptides, pharmaceutically active compounds, proteins, minerals, electrolytes.

11. The composition of claim 10, wherein the therapeutic substance is Vitamin C.

12. A method of preparing a hyper harmonized [D4 $(\Phi/\phi)$] form of a hydroxyl modified fullerene having a molecular formula of $C_{60}(OH)_x H_y \forall_z$ (where x is from 24 to 48, and y is from 0 to 24 and z is from 0 to 12); wherein the method comprises:

adding a hydroxylated fullerene to ultra-pure water form a mixture;

applying an oscillating magnetic field to the mixture at a temperature ranging from 30 to 50 C; wherein the magnetic force ranges from 0.25 T to 1.2 T; and forming a composition comprising a hyper harmonized form of a hydroxyl modified fullerene having a plurality of water layers surrounding the hyper harmonized form of the hydroxyl modified fullerene; wherein the plurality of water layers comprises from 4 water layers to 10 water layers, and wherein the composition has a remanent magnetism differing from a remanent magnetism of a non-harmonized $C_{60}(OH)_x H_y \forall_z$, where x is from 24 to 48, and y is from 0 to 24 and z is from 0 to 12, ranging from 10 nT to 12 nT.

13. The method of claim 12, wherein an amount of water molecules within the plurality of water layers ranges from 12 water molecules to about 6850 water molecules.

* * * * *